(12) United States Patent
Nolet et al.

(10) Patent No.: US 8,736,837 B2
(45) Date of Patent: May 27, 2014

(54) METHOD AND FLOW CELL FOR CHARACTERIZING PARTICLES BY MEANS OF NON-GAUSSIAN TEMPORAL SIGNALS

(71) Applicant: Handyem inc., Quebec, CA (US)

(72) Inventors: Dany Nolet, L'Ancienne-Lorette (CA); Alain Chandonnet, Quebec (CA); Michel Fortin, Quebec (CA)

(73) Assignee: Handyem Inc., Quebec (CA)

( * ) Notice: Subject to any disclaimer, the term of this patent is extended or adjusted under 35 U.S.C. 154(b) by 0 days.

(21) Appl. No.: 13/968,744

(22) Filed: Aug. 16, 2013

(65) Prior Publication Data

US 2013/0342837 A1   Dec. 26, 2013

Related U.S. Application Data

(63) Continuation of application No. 13/524,636, filed on Jun. 15, 2012.

(51) Int. Cl.
*G01N 21/00* (2006.01)

(52) U.S. Cl.
USPC .......................................... 356/338; 356/337

(58) Field of Classification Search
None
See application file for complete search history.

(56) References Cited

U.S. PATENT DOCUMENTS 7,843,561 B2    11/2010  Rich
8,536,542 B2 *   9/2013  Fortin et al. ................ 250/458.1

OTHER PUBLICATIONS

Brandwood, D. "Fourier Transforms in Radar and Signal Processing", chapter 3 Pulse Spectra, Artech House Publishers (Mar. 1, 2003) pp. 39-63.
Goulding, F.S., "Pulse-Shaping in Low-Noise Nuclear Amplifiers: A Physical Approach to Noise Analysis", Nuclear Instruments and Methods I00 (I972) pp. 493-504.
Goulding, F.S. et al., "Signal Processing for Semiconductor Detectors", IEEE 1981 Nuclear Science Symposium, San Francisco, CA, Oct. 21-23, 1981.
Wiesbeck, W. "Lecture Script—Radar System Engineering"; Universität Karlsruhe (TH) Research University, 13th Edition WS 2006/2007.

* cited by examiner

*Primary Examiner* — Gregory J Toatley
*Assistant Examiner* — Amanda Merlino
(74) *Attorney, Agent, or Firm* — BCF LLP

(57) ABSTRACT

The present disclosure relates to the field characterization of particles in a sample solution. More specifically, the present disclosure relates to a flow cell and a method for characterizing particles by means of collected non-Gaussian temporal signals. The present flow cell and method rely on an excitation fiber with a channel. The excitation fiber has a core for transporting an excitation light generated by a light source, and defines a channel through a portion of its core. The channel of the excitation fiber directs a flow of the sample solution. The excitation fiber, the channel and collection fibers characteristics are selected, proportioned and positioned to generate collected light with a non-Gaussian temporal intensity profile.

21 Claims, 12 Drawing Sheets

METHOD AND FLOW CELL FOR CHARACTERIZING PARTICLES BY MEANS OF NON-GAUSSIAN TEMPORAL SIGNALS

TECHNICAL FIELD

The present disclosure relates to the field of particles characterization in the context of flow cytometry. More specifically, the present disclosure relates to a method and a flow cell for characterizing particles by means of non-Gaussian temporal signal generation.

BACKGROUND

A flow cell is an apparatus for characterization of particles suspended in a sample solution. Particles sizes are generally in the range of ~0.5-40 µm. Particles are analyzed one-by-one with a typical count rate in the range of a few to thousand particles per second. Depending on its configuration, a flow cell could allow estimating different information about the particles such as presence, concentration, dimension, shape, vitality (in the case of cells), types of cells, structural and/or functional information, etc. Using a flow cell for sorting particles of different types in a heterogeneous solution is also possible.

Flow cytometers, which incorporate different configurations of flow cells, have been developed over the last 40 years. In general, a light source (i.e. a laser) emitting a light beam is focused on a fluid stream in the flow cell. The fluid flows at a predetermined rate in a capillary tube of the flow cell. Particles in the fluid stream cross the light during a brief interval of time, hence forming a short burst of temporal scattered light and fluorescence. A collection optics assembly, localized near or around the region where light and fluid intersect collects light emitted and/or scattered by the particles. The collected light is spectrally separated by a detection subassembly system, including for example various optical filters, and then received by detectors. Optical signal parameters of the collected light are measured by the detectors, and are processed by a computational system and/or electronic components.

For more than four decades, Gaussian optical pulses have been used in flow cytometry. The Gaussian optical pulses are the result of flow cell and flow cytometer design constraints: the use of spatially narrow laser beams dictated by optical density required for sufficient detection sensitivity; the spatial beam distribution of the laser, which is inherently Gaussian in shape, is translated in Gaussian pulses when particles transit at constant velocity through the beam; the requirement for high pulse rate generation hence short pulses to increase the throughput of the flow cytometer; noise source dominated by electrical noise; and analog circuitry that was well suited to perform Gaussian pulse filtering, followed by analog pulse detector, analog baseline tracking, peak detectors, log amplifiers and analog samplers, etc.

However, Gaussian optical pulses require important analog and digital treatment and signal processing resources, to extract characteristics of the particles in the solution. These required resources result in more complex and expensive flow cytometers. Furthermore, current flow cells and flow cytometers are limited by the inherent design constraints related to Gaussian signal generation, namely precise alignment of the laser beam with the position of the transiting particles, which is prone to misalignment and results in frequent and tedious alignment procedures for the users. There is therefore a need for an improved flow cell and method for characterizing particles in a solution by means of non-Gaussian temporal pulses to mitigate or eliminate these drawbacks.

SUMMARY

According to an aspect, the present disclosure relates to a flow cell for characterizing particles in a sample solution. The flow cell is adapted to be used with a light source generating an excitation light. The flow cell comprises an excitation fiber having a core for transporting the excitation light. The excitation fiber defines a channel substantially perpendicular and transversal to its core. The channel is adapted to receive a flow of the sample. The flow cell further comprises at least one collection fiber located in proximity of the channel. In presence of the excitation light, the at least one collection fiber collects light emitted or scattered by particles passing in the channel of the excitation fiber. The excitation and collection fibers characteristics are selected, proportioned and positioned in respect to each other to generate collected light of a non-Gaussian temporal intensity profile. More particularly, in some embodiments, the excitation and collection fibers characteristics are selected, proportioned and positioned in respect to each other to generate collected light of a non-Gaussian temporal intensity profile for a range of particles sizes, for a range of wavelengths, and/or for a range of particle sizes and a range of wavelengths.

In another aspect, the present relates to a method for characterizing particles in a sample solution. The method generates an excitation light that is transported within a core of an excitation fiber. A flow of the solution is directed within a channel of the excitation fiber, the channel being substantially perpendicular and transversal to its core. Light scattered or emitted by the particles flowing through the channel and intersecting the excitation light is collected by at least one collection fiber in proximity of the channel. The excitation fiber, its channel and the at least one collection fiber characteristics are selected, proportioned and positioned in respect to each other to generate collected light of a non-Gaussian temporal intensity profile. More particularly, in some embodiments, the excitation fiber and/or its channel and/or the at least one collection fiber is/are relatively proportioned and positioned to obtain collected light of a non-Gaussian temporal intensity profile for a range of particles sizes, for a range of wavelengths, and/or for a range of particle sizes and a range of wavelengths.

The foregoing and other features of the present flow cell and method will become more apparent upon reading of the following non-restrictive description of illustrative embodiments thereof, given by way of example only with references to the accompanying drawings.

BRIEF DESCRIPTION OF THE DRAWINGS

Embodiments of the disclosure will be described by way of examples only, with reference to the accompanying drawings, in which.

DETAILED DESCRIPTION

Figure 1:
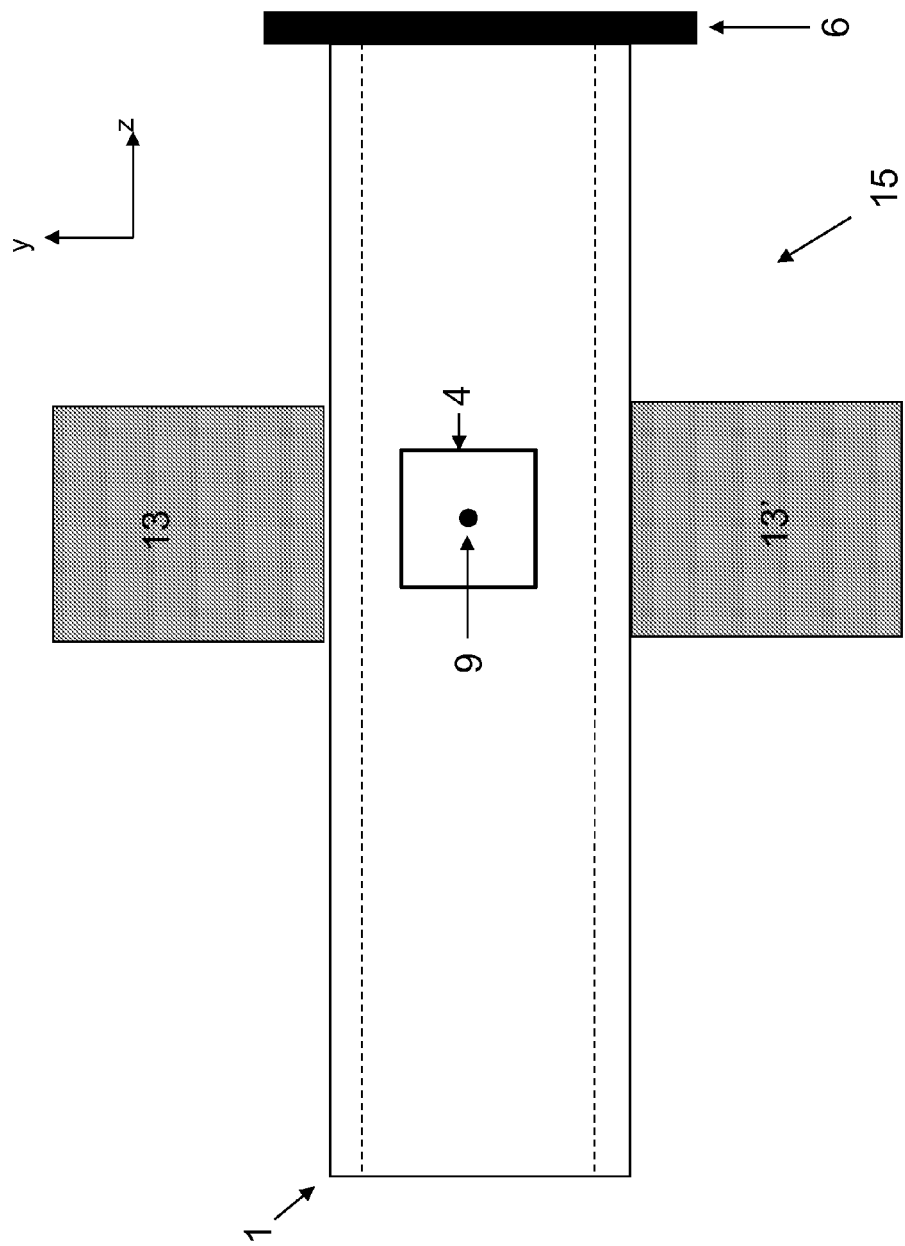
FIG. 1 is a schematic representation of a flow cell in the y-z plane.

The following terminology is used throughout the present disclosure, and is meant to be interpreted as follows:

Flow cell: apparatus for characterizing particles in suspension in a sample solution, the apparatus relying on principles of light propagation, light scattering and/or fluorescence.

Light scattering: physical process by which light at a specific wavelength deviates from its path after interacting with a perturbation of the medium it is propagating in, such as a particle, a variation of the index of refraction, an interface, etc. . . . ).

Fluorescence: light emitted after absorption of incident light by a medium or particle, where the wavelength of the light emitted is longer (lower energy) than the wavelength of the incident light (higher energy).

Excitation zone: intersection of the excitation light and sample solution.

Impulsion or pulse: time-dependence of the intensity of detected light.

Optical fiber: Substantially transparent medium propagating and guiding light within its core.

Core: central part of an optical fiber wherein light is mostly localized during its propagation.

Cladding: peripheral section of an optical fiber.

Excitation fiber: optical fiber transporting the excitation light from a light source to the excitation zone.

Sample solution: fluid containing suspended particles.

Signal processing system: assembly of electronic components and/or processor(s) and/or software(s) to extract at least one particle characteristic from collected optical signal parameters.

Collection fiber: optical fiber located in proximity of the excitation zone, to collect light scattered or emitted by the particles in the excitation zone.

Collection window: End face of the collection fiber facing the excitation zone to collect light scattered or emitted by the particles.

Non-Gaussian temporal signal: impulsion having a rise time, a fall time, and optionally a plateau in-between. Examples of non-Gaussian temporal signals, without being limitative, include symmetric or asymmetric trapezoidal temporal signals, triangular temporal signals and quasi-square temporal signals.

The present description discloses a flow cell and a method for characterizing particles in a sample solution. More particularly, the present flow cell and method are designed so as to generate light collected of non-Gaussian temporal intensity profile. The present also relates to an apparatus, such as for example a flow cytometer, using the present flow cell, and adapted to detect and process non-Gaussian temporal signals to characterize particles in a sample solution.

Flow Cell

In an aspect, the present relates to a flow cell. The present flow cell is adapted to be connected to a light source, which generates an excitation light. The flow cell comprises an excitation fiber having a core for transporting the excitation light. The excitation fiber defines a channel transversal to its core across a portion of its length. The channel is sized to direct a flow of a sample solution comprising particles in suspension therein. The flow cell further comprises at least one collection fiber for collecting light scattered or emitted by the particles flowing through the channel, upon excitation by the excitation light. The at least one collection fiber of the flow cell is adapted to connect to a collection optics system if required, and ultimately to connect to an optical detection system for transforming the light collected into an electrical signal. The excitation fiber, the channel of the excitation fiber and the at least one collection fiber characteristics are selected, proportioned and positioned in respect to each other so as to obtain light collected having a non-Gaussian temporal intensity profile. In specific embodiments of the present flow cell, the excitation fiber, the channel of the excitation fiber and the at least one collection fiber characteristics are selected, proportioned and positioned in respect to each other so as to obtain light collected with a non-Gaussian temporal intensity profile for a range of particle sizes, or for a range of wavelengths, or for both a range of particle sizes and a range of wavelengths.

Reference is now made to FIG. 1, which schematically represents a flow cell 15. The flow cell 15 comprises an excitation fiber 1 defining a channel 4 transversal through its core to direct particles 9. The excitation fiber may further have an end opposite to a light source, comprising a reflective material 6. The flow cell further comprises at least one collection fiber 13. The collection fiber 13 is located next to the excitation fiber, adjacent to the channel 4. In the embodiment shown on FIG. 1, two collection fibers 13 and 13' are shown located diametrically opposed on sides of the channel 4 of the excitation fiber. More collection fibers 13 could be used, depending on the implementation, precision desired and processing capabilities. The main advantage of using symmetrically placed collection fibers is to mitigate the dependency of the scattered or emitted signal by the particles on its specific path within the channel of the excitation fiber.

The flow cell 15 can be implemented as a module ready to be inserted within an apparatus. Alternatively, the excitation fiber 1 and the collection fiber(s) 13 may be implemented as a removable flow cell cartridge for handy insertion and removal within the module. Providing a removable flow cell facilitates maintenance, increases versatility and improves reliability of the flow cytometer. The flow cell 15 can have different forms and dimensions.

Excitation Fiber

Figure 2:
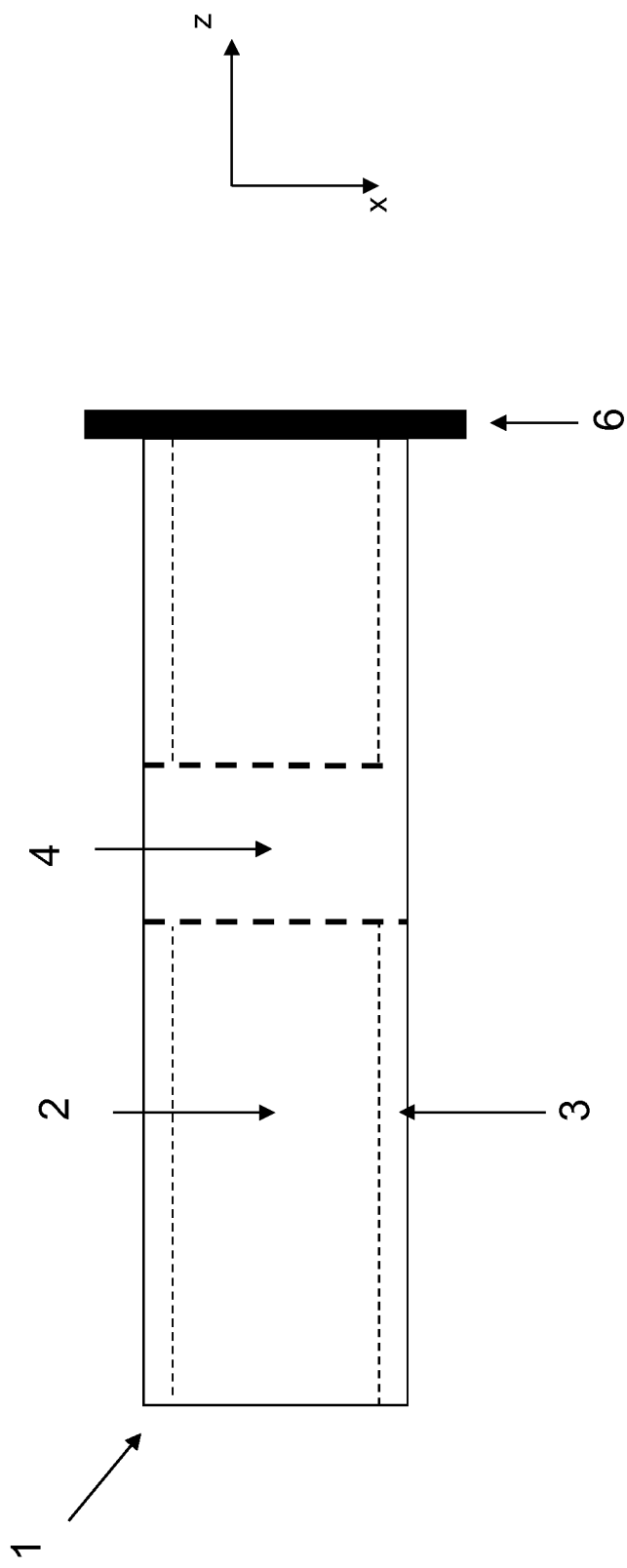
FIG. 2 is a schematic representation of the present excitation fiber in an x-z plane.
Figure 3:
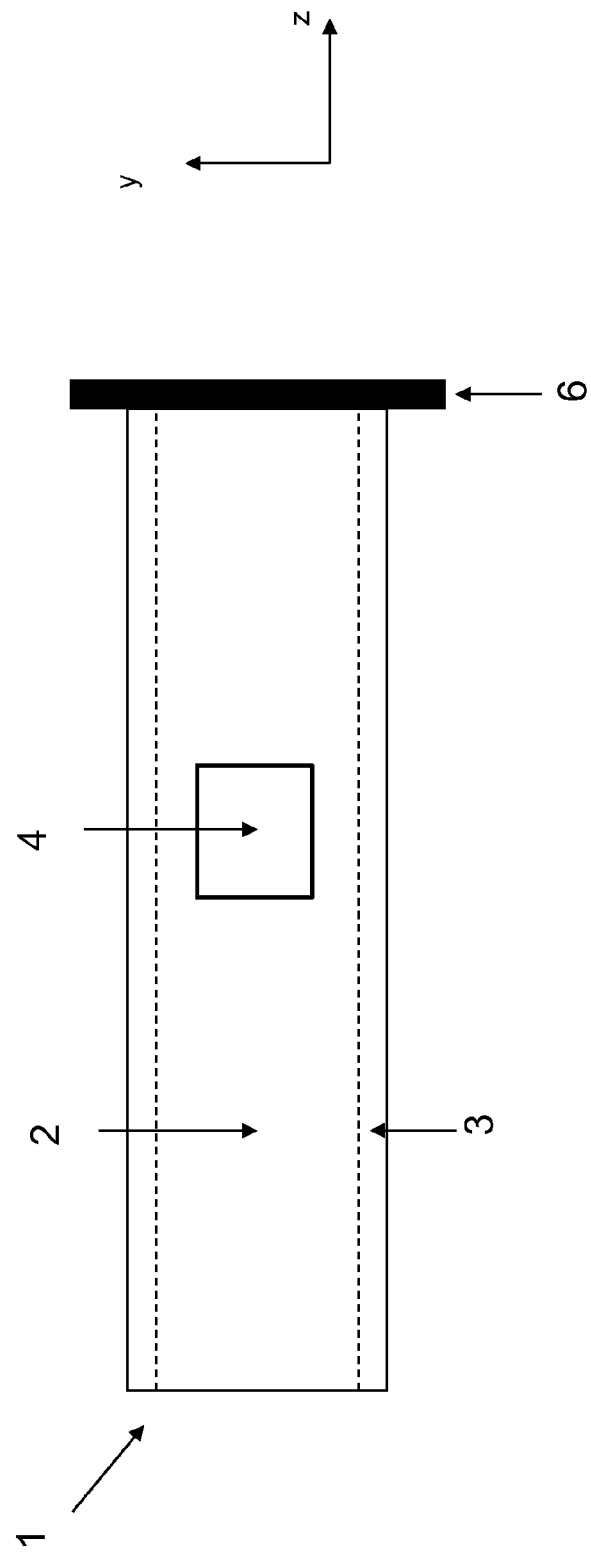
FIG. 3 is a schematic representation a square-shaped channel.

Reference is concurrently made to FIG. 2, which depicts a schematic representation of the present excitation fiber in an x-z plane, and FIG. 3, which is a schematic representation of a square shaped channel.

The excitation fiber 1 is an optical fiber typically comprising a core 2 that is surrounded by a cladding 3. Excitation light generated by a light source is transported by the excitation fiber 1. During transport, the excitation light is concentrated in the core 2 of the excitation fiber 1. The excitation fiber is a multi-mode fiber. The excitation fiber may be made of any type of material well known in the fiber optic industry. The excitation fiber 1 defines a channel 4 transversal to and through its core, through a portion of its length. The channel 4 receives the sample solution comprising the particles in suspension therein. The channel 4 may receive the sample solution by means of any known method, such as a capillary tube or a microfluidic system, not shown on FIG. 2 for simplicity purposes. The channel 4 directs the sample solution through the excitation fiber 1, from side to side. The channel 4 is shaped so as to receive and efficiently illuminate the sample solution and particles therein at an intersection thereof, called an excitation zone.

The channel 4 may be realized by any technique known to the fiber optic industry, such as for example laser micromachining techniques. The channel 4 may define various shapes (circular, rectangular, square or irregular), a constant section, may define a slightly irregular section, or a varying section through the excitation fiber 1. The channel 4 may have a slightly tapered exterior profile to facilitate insertion of the sample solution therein.

A reflective medium 6, such as for example a mirror, a reflective surface, a metal or a dielectric coating, may be affixed to an end of the excitation fiber 3 opposite to the light source, so as to reflect the excitation light having passed once through the sample solution, and thereby increase the excitation light present within the excitation zone.

Figure 4:
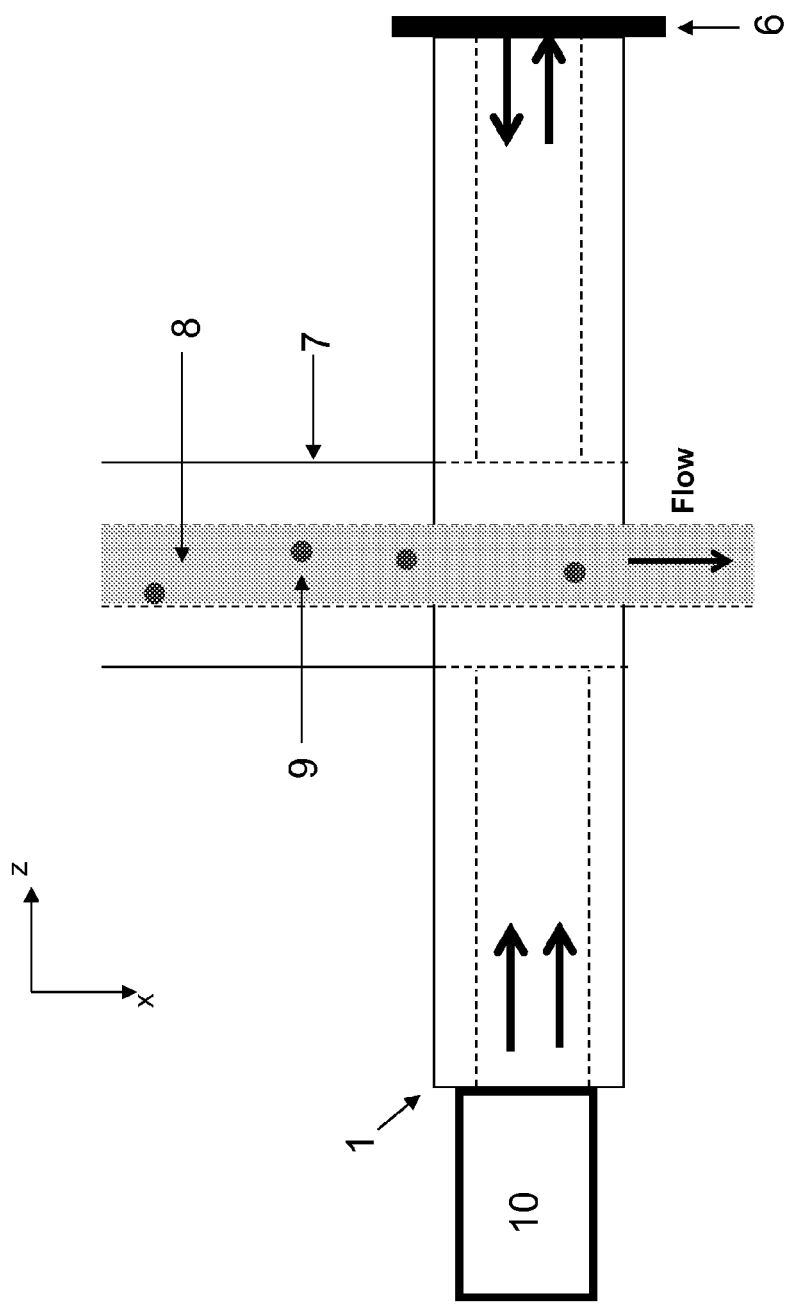
FIG. 4 is a schematic representation of the present excitation fiber in which a flow of sample solution is channeled.

Reference is now concurrently made to FIGS. 1-4, where FIG. 4 is a schematic representation of the excitation fiber 1, in which the sample solution is directed in the channel 4. In this particular example, a capillary tube 7 is used to introduce the sample solution in the channel 4 of the excitation fiber 1. Those skilled in the art will understand that matching of the shape and size of the channel 4 and exterior of the capillary tube is required to transfer of the sample solution into the channel 4. Another capillary tube (not shown) may also be provided on the other side of the channel so as to collect the sample solution that has passed through the channel of the excitation fiber.

The channel 4 directs the flow of sample solution through the excitation fiber 1. The sample solution 8 may be a fluid in which particles 9 are in suspension. For example, the sample solution could consist of blood containing blood cells. Signal processing algorithms may be used to distinguish individual particles 9 transiting in channel 4 when more than one particle 9 is simultaneously present in channel 4. It is also possible to define a regimen of concentration of particles in suspension in the sample solution using Poisson law, to maximize the statistical likelihood of having only one particle at a time into the excitation zone.

Flow Cytometer

Figure 5:
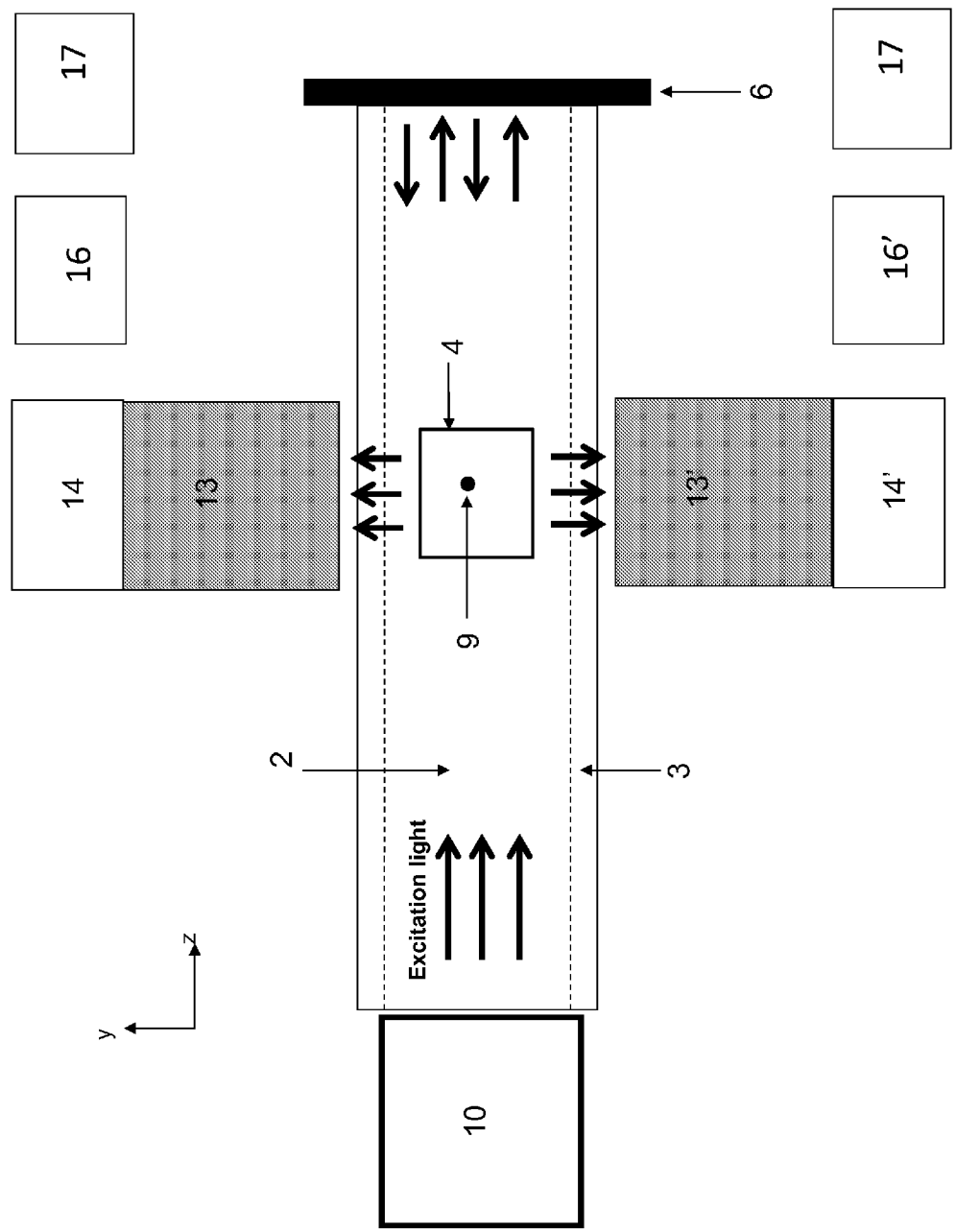
FIG. 5 is a schematic representation of the present flow cell in the y-z plane, in the context of an exemplary apparatus.

Reference is now made to FIG. 5, which is a schematic representation of the present flow cell in an exemplary apparatus: a flow cytometer. The flow cytometer is used as an example only, as the present flow cell can be used and implemented in various other types of apparatuses such as, for example, a cell counter.

The present flow cell is thus optically connected to a light source 10. The light source 10 is connected either directly or by means of a coupling mechanism (not shown) to an extremity of the excitation fiber. Any means of coupling known in the art may be used such as, for example, bulk lenses, fiber optic mating connectors or mechanical or fusion splicing.

The light source 10 generates the excitation light to be transported by the excitation fiber 1. Examples of light sources that can be used include lasers and light-emitting diodes, typically, for example, lasers of various wavelengths such as 405, 473, 488, 532, 560, 638 nm etc.

In the schematic representation of FIG. 5, the flow cell comprises the excitation fiber 1 and two collection fibers 13 and 13' adjacent the channel 4 of the excitation fiber, diametrically opposed. The collection fibers 13 and 13' collect light emitted or scattered by particles flowing through the channel, in presence of excitation light.

The excitation zone corresponds to an intersection where the excitation light (including the light reflected if a reflective surface is used) and the sample solution in the channel of the excitation fiber meet. The excitation light illuminates the excitation zone. As the sample solution flows through the channel, some of the excitation light interacts with the particle. The excitation light scatters upon interaction with the particle. If a fluorophore is used in the sample solution, for example for cell-labeling, interaction of the excitation light with an excitable fluorophore results in light emitted in the form of fluorescence by the fluorophore at a different wavelength than the excitation light.

In FIG. 5, vertical arrows correspond to the light scattered, and if a fluorophore is present also to light emitted, by the illumination of the particle flowing in the channel. Those skilled in the art will understand that scattered and emitted light does not follow necessarily the vertical arrows, and that only a portion of the scattered and emitted light does travel along the vertical lines shown in FIG. 5. Thus the vertical lines should be interpreted as a general direction of interest rather than an absolute direction.

Depending on the requirements of the apparatus, the collection fibers 13 and 13' may further be connected to a collection optics system 14 and 14' such as for example filters and/or analog components. The collection optics system 14 and 14' may comprise optical filters to separate the light scattered from the light emitted. The collection optic system 14 and 14' are connected to one or separate optical detection systems 16. The optical detection systems 16 receive the light collected from the collection optic system if used, or directly from the collection fibers 13 and 13' if no collection system is used. The optical detection systems 16 transform the collected light into a corresponding electric signal. The electric signal is afterwards provided to a signal processing system 17, which determines characteristics of the particles as described later.

Although two optical detection systems 16 and 16' are shown on FIG. 5 the present flow cytometer is not limited to such an implementation. For example, one of the optical detection systems 16 could be connected to multiple optical collection systems 14 and 14', or directly to multiple collection fibers 13 and 13'.

Light Scattered and Emitted

Figure 6A:
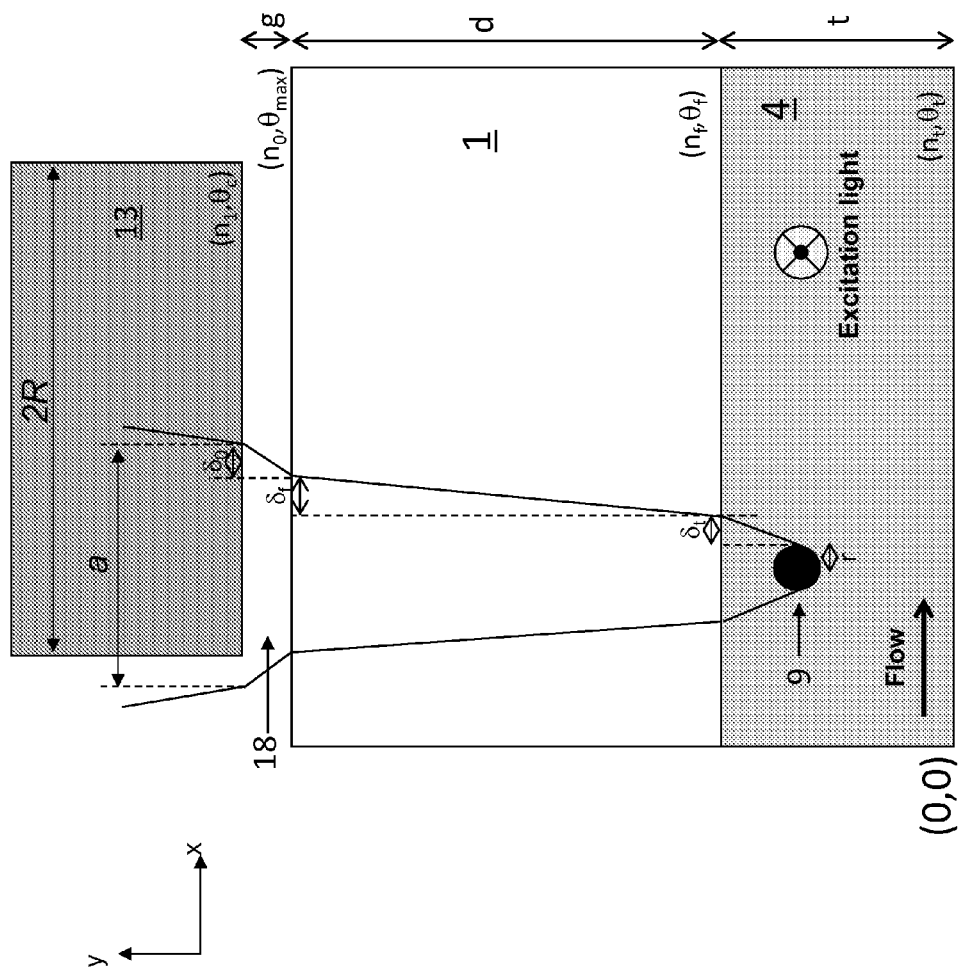
FIGS. 6A and 6B are a partial schematic representation of portion of the present flow cell superimposed to a tracing of an optical path representing light scattered or emitted by fluorescence from a particle.
Figure 6B:
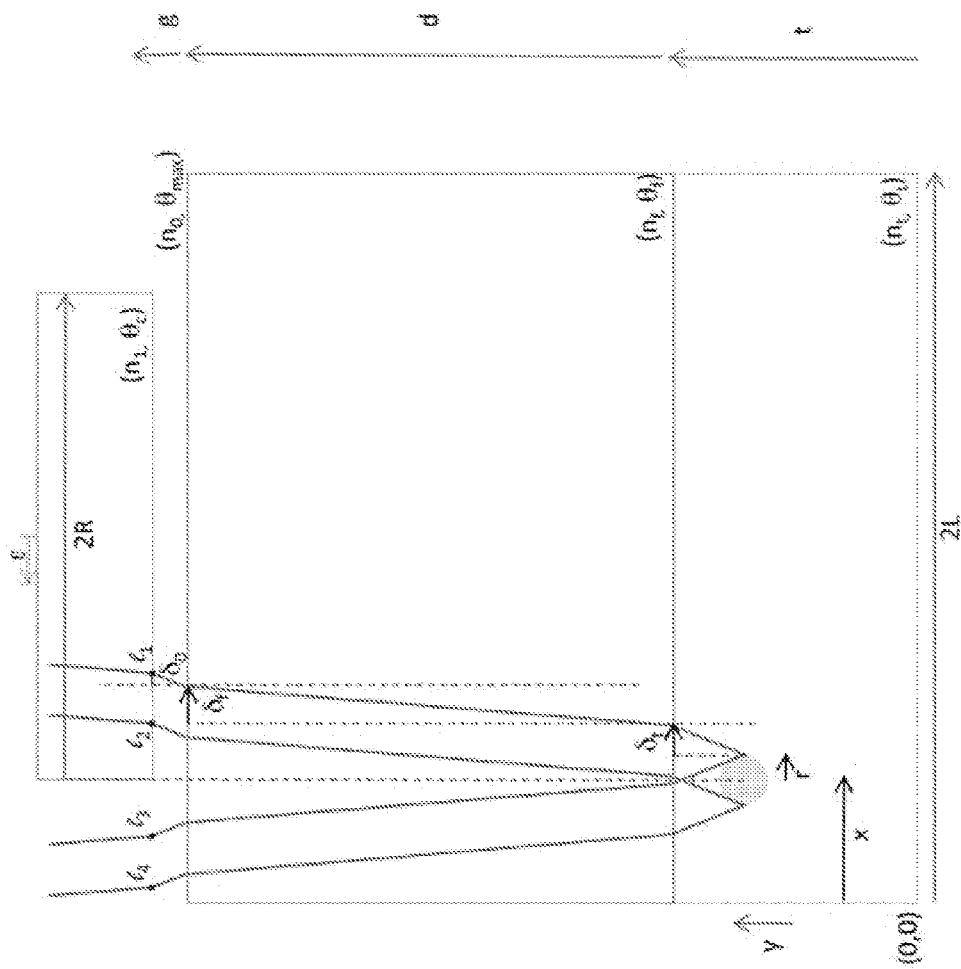

Reference is now made to FIGS. 6A and 6B, which are graphs depicting scattered light, or alternatively if a fluorophore is used, emitted light. For simplicity purposes, only one particle is depicted, but the present flow cell and method are adapted to characterize multiple particles consecutively. For reference purposes, the particle 9 is moving from left to right along the x-axis, and the excitation light is in the z-axis, and thus perpendicular to the graph. In the present Light scattered and emitted section, only reference to scattered light will be discussed for the sake of simplicity. However, this discussion is general in nature and applies equally well to light emitted from fluorophores attached to the particles 9.

When the excitation light interacts with the particle 9 of radius r, the excitation light is scattered by the particle. The light scattered by the particle continues its course in the channel 4 and transversally crosses part of the excitation fiber 1 which in general deviates its path, due to a difference in refractive index between the sample solution in the channel 4 and the excitation fiber 1. The light scattered exits the excitation fiber 1 to enter a zone 18 between the excitation zone 1 and the collection fiber 13, which may cause another deviation in presence of another difference in refractive index, before entering the collection fiber 13. At the entrance of the collection fiber 13, the light scattered allowed to enter and be guided by the collection fiber forms a circle having a maximum diameter of value a defined by the numerical aperture (i.e. maximum cone of acceptance) of the collection fiber, while 2R corresponds to the geometrical diameter of the collection fiber 13. The amount of scattered light by particle 9 coupled in the collection fiber can hence be described as the overlapping intersection of two circles of diameter a and 2R respectively.

Figure 7:
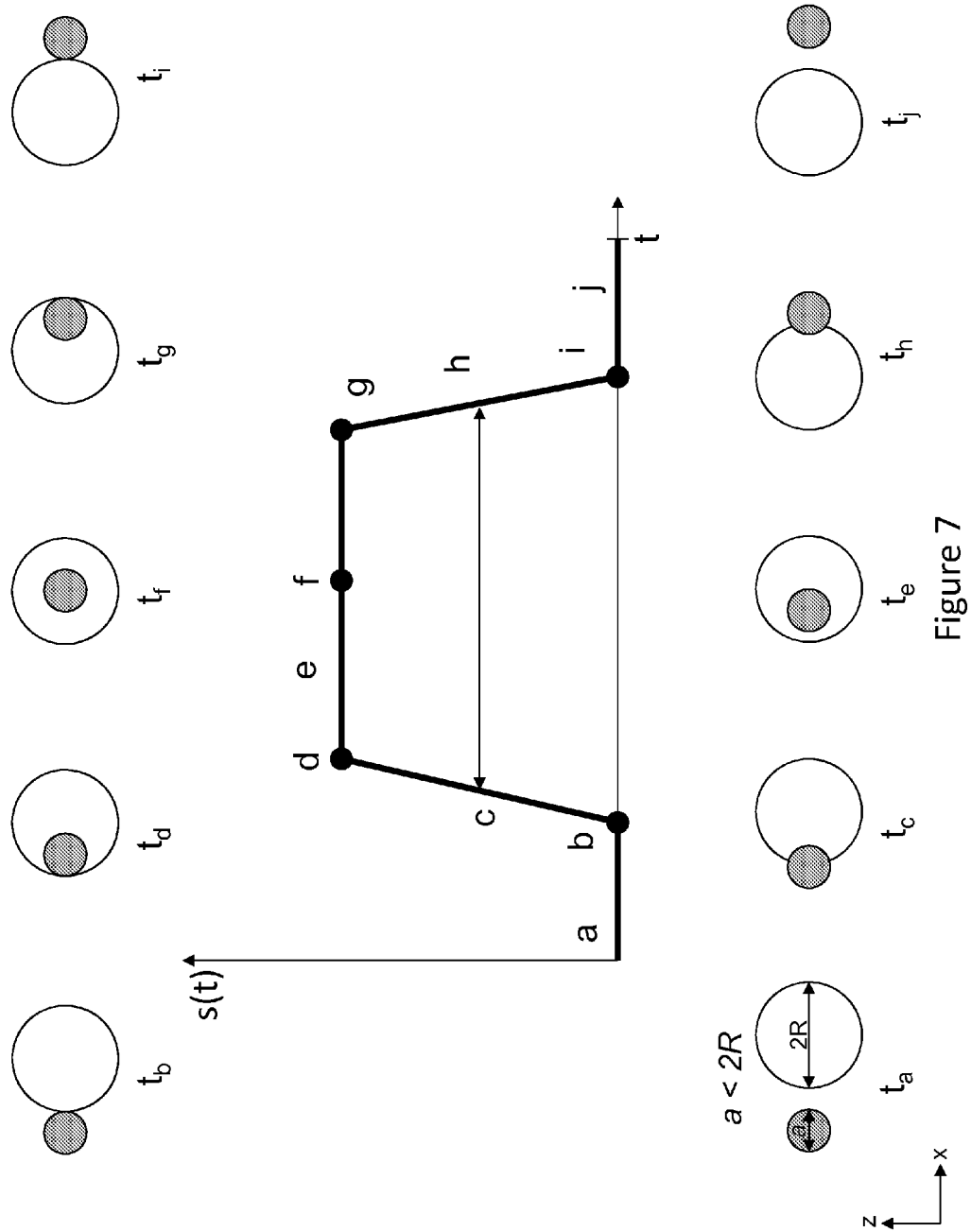
FIG. 7 is a graph representing light collected for a particle flowing in the center of the channel (y=0) of the excitation fiber where a<2R.
Figure 8:
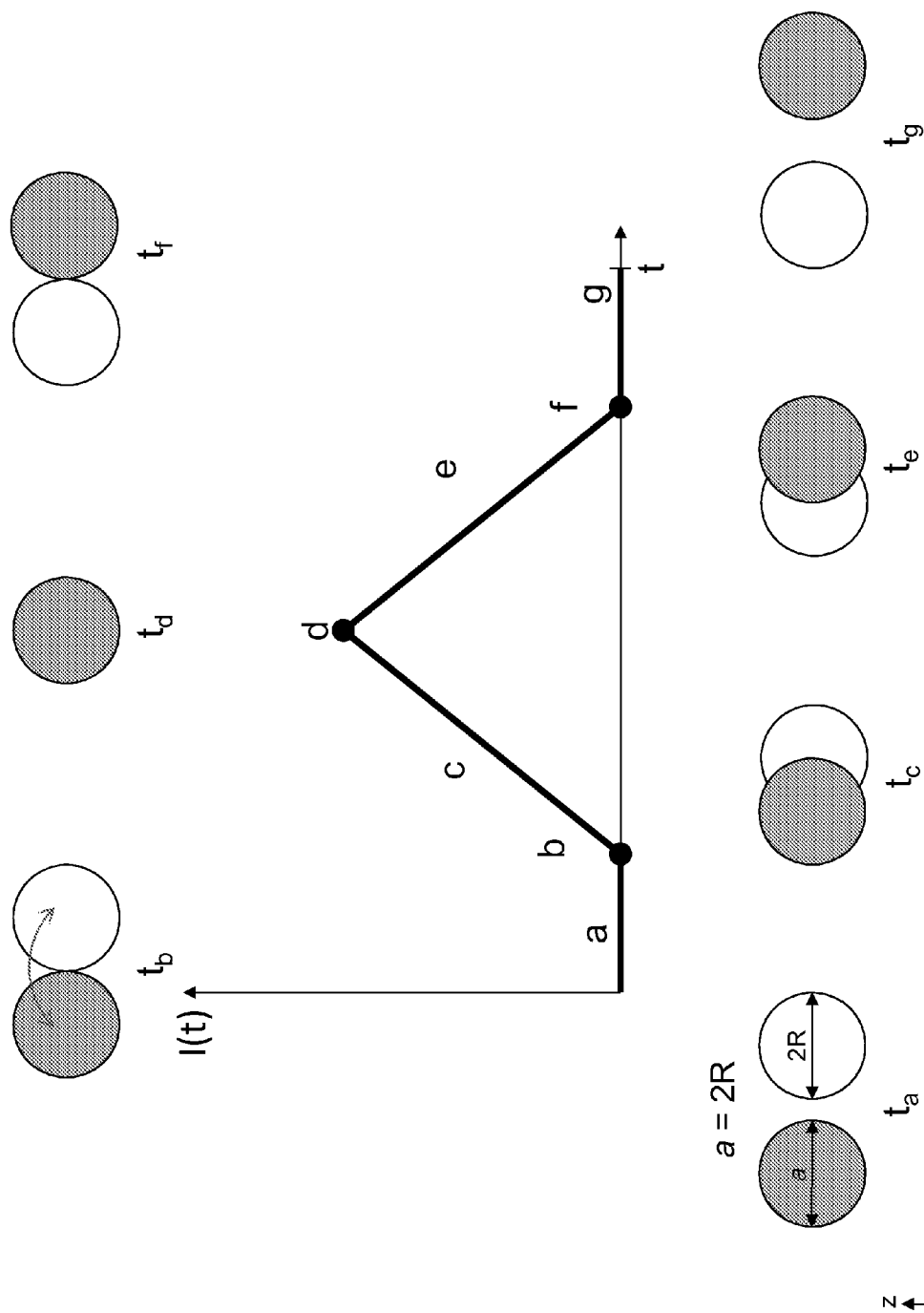
FIG. 8 is a graph representing light collected for a particle flowing in the center of the channel (y=0) of the excitation fiber where a=2R.

Reference is now concurrently made to FIGS. 6A and 6B, 7 and 8, where FIGS. 7 and 8 are conceptual graphical representations of the light collected by the collection fiber 13 of FIGS. 6A and 6B, upon movement of the particle 9 in the channel 4, for two different sizes of particles 9.

In FIG. 7, the collection fiber 13 has a diameter of value 2R, where 2R is greater than a. Upon movement along the x-axis of the particle 9, the light scattered by the particle 9 is collected at the collection fiber 13. Relative movement of the particle 9 with respect to the collection fiber 13 is depicted on FIG. 7 on the top and bottom, for time $t_a$ to $t_j$. For each instant $t_a$ to $t_j$, the small circle a corresponds to the light scattered allowed to be guided by the collection fiber, while the larger circle corresponds to the geometrical diameter of the collection fiber, identified as 2R.

Upon movement along the x-axis of the particle 9 within the channel 4, the light collected gradually increases in the collection fiber 13. Thus at instant $t_a$, there is no light collected. At instant $t_b$, the cone of allowed scattered light starts overlapping the end face of the collection fiber 13. At $t_c$, the light collected by the collection fiber increases, as the particle 9 moves in the channel. At $t_d$, the light collected reaches its maximum intensity. The maximum intensity of light collected is maintained while the particle continues its movement across the channel because the area of the scattered light underfills the area of the collection fiber, until the particles reaches the other extremity of the collection fiber end face. The intensity of the light collected then gradually decreases, from instant $t_g$ to $t_i$, where it reaches its minimum, and is no longer collected.

FIG. 8 is a similar graph as FIG. 7, for a collection fiber 13 having a diameter of value 2R, where 2R is equal to a. In FIG. 8, the light collected peaks at $t_d$, but cannot form a plateau because area a and 2R overlap only at that specific position.

Figure 9:
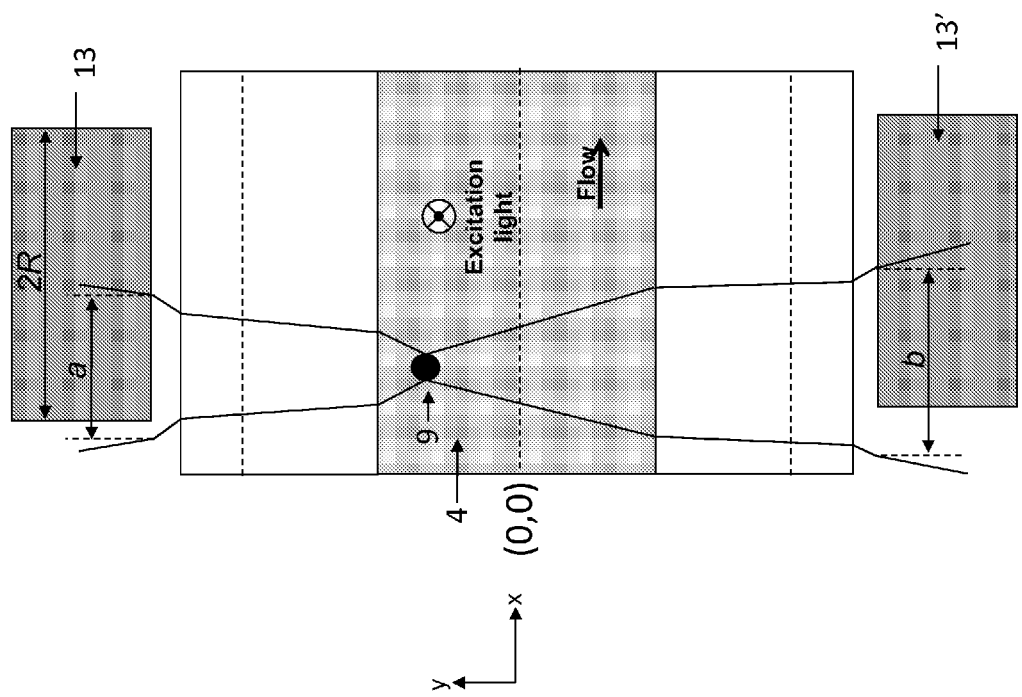
FIG. 9 is a partial schematic representation of the present flow cell with two collecting fibers, superimposed to a tracing of an optical path representing light scattered or emitted by fluorescence from a particle.

Reference is now made to FIG. 9, which is a partial schematic representation of the present flow cell with two collecting fibers, superimposed to a tracing of an optical path representing light scattered from a particle. The particle 9 of radius r (with its center at coordinate x) flows in the channel 4 along the x-direction, and is off-centered (y≠0) in the channel 4. The light scattered by the off-centered particle produces cones of collected light at the collection fibers 13 and 13' of different diameters. Thus the diameter of the light collected at the collection fiber closest to the particle is of a smaller radius than the diameter of the light collected at the collection fiber farther from the particle (a≠b).

Non-Gaussian Temporal Light Collected—One Collection Fiber

To generate light collected of non-Gaussian temporal intensity profile, the relative optical properties, proportions and positions between the excitation fiber, the channel and the collection fiber must be carefully considered in details Prospective determination of the relative optical properties, proportions and positions between the excitation fiber, the channel and the collection fiber requires the following formalism.

Snell's law establishes that:

$$n_1 \sin\left(\frac{\pi}{2} - \theta_c\right) = n_0 \sin\theta_{max} = n_f \sin\theta_f = n_t \sin\theta_t \quad (1)$$

where:
$\theta_c$=critical angle of total internal reflection in the collection fiber;
$\theta_{max}$=maximum acceptance angle of light entry in the collection fiber;

$$n_0 \sin\theta_{max} = NA = \sqrt{n_1^2 - n_2^2} \quad (2)$$

$n_1$=collection fiber core refractive index;
$n_2$=collection fiber cladding refractive index;
$n_0$=refractive index of the medium between the collection fiber and the excitation fiber;
$n_f$=excitation fiber core refractive index;
$n_t$=refractive index of the sample solution within the excitation fiber channel; and
∈=collection fibers relative alignment error when more than one collection fiber is used.

Thus, the following equations can be obtained from straightforward symmetrical considerations using (1) and (2):

$$\delta_t = (t - y)\tan\theta_t = (t - y)\frac{NA}{\sqrt{n_t^2 - NA^2}} \quad (3)$$

$$\delta_f = d\tan\theta_f = d\frac{NA}{\sqrt{n_f^2 - NA^2}} \quad (4)$$

$$\delta_0 = g\tan\theta_0 = g\frac{NA}{\sqrt{n_0^2 - NA^2}} \quad (5)$$

It is possible to calculate positions of loci $l_1$ to $l_4$, shown on FIG. 6B, to qualitatively determine a collection regime of the scattered/emitted light collected for the particle of radius r moving along the x-axis, at a position y relative to the aperture of radius t and length 2L, through the excitation fiber cladding of thickness d and a distance g between the collection fiber of radius R and the excitation fiber.

$$l_1 = x + r + \delta_t + \delta_f + \delta_0 \quad (6)$$

$$l_2 = x - r + \delta_t + \delta_f + \delta_0 \quad (7)$$

$$l_3 = x + r - \delta_t - \delta_f - \delta_0 \quad (8)$$

$$l_4 = x - r - \delta_t - \delta_f - \delta_0 \quad (9)$$

Since the particle must be within the aperture to be illuminated, and in the case of a fluorophore emitting light isotropically, the following conditions must be applied to the loci. Conditions on $l_1$ $l_1$:

$$x \geq -r \quad (10)$$

$$x + r + \delta_t \leq 2L \quad (11)$$

The light scattered and/or emitted corresponding to $l_1$ may, by total internal reflection, be directed to the collection fiber by a superior (or inferior) surface of the excitation fiber, so that if $x+r+\delta_t+\delta_f \leq 2L$ then $l_1=x+r+\delta_t+\delta_f+\delta_0$; and if $x+r+\delta_t+\delta_f > 2L$ then $l_1=|x+r+\delta_t+\delta_f+\delta_0|$.

Conditions on $l_2$ $l_2$ $l_2$:

$$x \geq r \qquad (12)$$

$$x-r+\delta_t \leq 2L \qquad (13)$$

The light scattered and/or emitted corresponding to $l_2$ may, by total internal reflection, be directed to the collection fiber by a superior (or inferior) surface of the excitation fiber, so that:

if $x-r+\delta_t+\delta_f \leq 2L$ then $l_2=x-r+\delta_t+\delta_f+\delta_0$; and if $x-r+\delta_t+\delta_f > 2L$ then $l_2=|x-r+\delta_t+\delta_f+\delta_0|$.

Conditions on $l_3$ $l_3$:

$$x+r-\delta_t \geq 0 \qquad (14)$$

The light scattered and/or emitted corresponding to $l_3$ $l_3$ may, by total internal reflection, be directed to the collection fiber by a superior (or inferior) surface of the excitation fiber, so that:

if $x+r-\delta_t-\delta_f \geq 0$ then $l_3=x+r-\delta_t-\delta_f-\delta_0$; and if $x+r-\delta_t-\delta_f < 0$ then $l_3=|x+r-\delta_t-\delta_f-\delta_0|$.

Conditions on $l_4$ $l_4$:

$$x-r-\delta_t \geq 0 \qquad (15)$$

The light scattered and/or emitted corresponding to $l_4$ may, by total internal reflection, be directed to the collection fiber by a superior (or inferior) surface of the excitation fiber, so that:

if $x-r-\delta_t-\delta_f \geq 0$ then $l_4=x+r-\delta_t-\delta_f-\delta_0$; and if $x-r-\delta_t-\delta_f < 0$ then $l_4=|x-r-\delta_t-\delta_f-\delta_0|$.

Intensity Regime

The collection fiber will not collect any light scattered or emitted when the four loci are outside its diameter, i.e.:

$$(L-\in+R) < (l_1,l_2,l_3,l_4) < (L-\in-R) \qquad (16)$$

for a collection fiber centered at $(L-\in e)$.

This equation translates into:

$$l_1 < (L-\in-R) \text{ or } l_4 > (L-\in+R) \qquad (17)$$

Which demonstrates that a position $x_1$ $x_1$ corresponding to the beginning of the collection of light scattered or emitted (represented as $t_b$ in FIG. 7), is established by:

$$l_1=(L-\in-R)=x_1+r+\delta_t+\delta_f+\delta_0 \qquad (18)$$

$$x_1=(L-\in-R)-r-\delta_t-\delta_f-\delta_0 \qquad (19)$$

And a position $x_4$ $x_4$ corresponding to an end of the collection of the light scattered or emitted, (corresponding to $t_i$ in FIG. 7) is defined as follows:

$$l_4=(L-\in-R)=x_4-r-\delta_t-\delta_f-\delta_0 \qquad (20)$$

$$x_4=(L-\in+R)+r+\delta_t+\delta_f+\delta_0 \qquad (21)$$

Maximum intensity of the collected light scattered or emitted will be when the four loci are within the end face of the collection fiber, which is established by:

$$(L-\in-R) \leq (l_1,l_2,l_3,l_4) \leq (L-\in+R) \qquad (22)$$

for a collection fiber centered at $(L-\in)$.

This equation translates into:

$$l_4 \geq (L-\in-R) \text{ or } l_1 \leq (L-\in+R) \qquad (23)$$

Thus a position $x'_4$ $x'_4$ corresponding to the beginning of a plateau of maximum intensity (represented as $t_d$ on FIG. 7) may be obtained by:

$$l'_4=(L-\in-R)=x'_4-r-\delta_t-\delta_f-\delta_0 \qquad (24)$$

$$x'_4=(L-\in-R)+r+\delta_t+\delta_f+\delta_0 \qquad (25)$$

A value $x'_1$ $x'_1$ corresponding to the end of the plateau of maximum intensity (represented as $t_g$ on FIG. 7) may be obtained by:

$$l'_1=(L-\in+R)=x'_1+r+\delta_t+\delta_f+\delta_0 \qquad (26)$$

$$x'_1=(L-\in+R)-r-\delta_t-\delta_f-\delta_0 \qquad (27)$$

The total length $\gamma_{total}$ of the collected light scattered or emitted by the particle, as well as the length of the plateau of maximum intensity $\gamma_{plateau}$ $\gamma_{plateau}$ may be obtained as follows:

$$\gamma_{total}=x_4-x_1=2R+2(r+\delta_t+\delta_f+\delta_0) \qquad (28)$$

$$\gamma_{plateau}=x'_1-x'_4=2R-2(r+\delta_t+\delta_f+\delta_0) \qquad (29)$$

The total length $\gamma_{total}$ of the collected light scattered or emitted by the particle, as well as the length of the plateau of maximum intensity $\gamma_{plateau}$ $\gamma_{plateau}$ may be converted into time duration, using a flow rate for the sample solution and particles circulating through the aperture of the excitation fiber. Thus, the duration $\tau_{total}$ of the light collected and $\tau_{plateau}$ of the plateau of maximum intensity are expressed as a function of the flow rate of the sample solution and particles $v_{flux}$ $v_{flux}$ as follows:

$$\tau_{total} = \frac{\gamma_{total}}{v_{flux}} \qquad (30)$$

$$\tau_{plateau} = \frac{\gamma_{plateau}}{v_{flux}} \qquad (31)$$

The case where $\gamma_{plateau}=x'_1-x'_4=0$ $\gamma_{plateau}=x'_1-x'_4=0$ corresponds to collected light scattered or emitted having a triangular temporal profile, and represents the limiting case of a trapeze without a plateau.

Non-Gaussian Temporal Light Collected—Two Opposite Collection Fibers

The previous mathematical equations relate to one collection fiber. When two diametrically opposed collection fibers are used with one optical detection system, the optical detection system detects the sum of the light collected by the two collection fibers, such as shown in FIG. 9. Thus the equations previously presented apply to a first collection fiber, and equations for a second collection fiber may be obtained by substituting (t−y) by (y) in equation (3) and use the same equations. Thus (3a) corresponds to the equation applicable to the first collection fiber, while (3b) corresponds to the equivalent equation for the second collection fiber, as follows:

$$\delta_t^{(1)} = (t-y)\tan\theta_t = (t-y)\frac{NA^{(1)}}{\sqrt{n_t^2-NA^{(1)2}}} \qquad (3a)$$

-continued $$\delta_t^{(2)} = (y)\tan\theta_t = y\frac{NA^{(2)}}{\sqrt{n_t^2 - NA^{(2)^2}}} \quad (3b)$$

Generalizing for different values of d, g and NA for the two collection fibers:

$$\delta_f^{(1)} = d^{(1)}\tan\theta_f^{(1)} = d^{(1)}\frac{NA^{(1)}}{\sqrt{n_f^2 - NA^{(1)^2}}} \quad (4a)$$

$$\delta_f^{(2)} = d^{(2)}\tan\theta_f^{(2)} = d^{(2)}\frac{NA^{(2)}}{\sqrt{n_f^2 - NA^{(2)^2}}} \quad (4b)$$

$$\delta_0^{(1)} = g^{(1)}\tan\theta_0^{(1)} = g^{(1)}\frac{NA^{(1)}}{\sqrt{n_0^2 - NA^{(1)^2}}} \quad (5a)$$

$$\delta_0^{(2)} = g^{(2)}\tan\theta_0^{(2)} = g^{(2)}\frac{NA^{(2)}}{\sqrt{n_0^2 - NA^{(2)^2}}} \quad (5b)$$

Thus the following equations may be obtained for the first and second collection fibers:

$$\gamma_{total}^{(1)} = x_4^{(1)} - x_1^{(1)} = 2R^{(1)} + 2(r^{(1)} + \delta_t^{(1)} + \delta_f^{(1)} + \delta_0^{(1)}) \quad (28a)$$

$$\gamma_{total}^{(2)} = x_4^{(2)} - x_1^{(2)} = 2R^{(2)} + 2(r^{(2)} + \delta_t^{(2)} + \delta_f^{(2)} + \delta_0^{(2)}) \quad (28b)$$

$$\gamma_{plateau}^{(1)} = x'_1{}^{(1)} - x'_4{}^{(1)} = 2R^{(1)} - 2(r^{(1)} + \delta_t^{(1)} + \delta_f^{(1)} + \delta_0^{(1)}) \quad (29a)$$

$$\gamma_{plateau}^{(2)} = x'_1{}^{(2)} - x'_4{}^{(2)} = 2R^{(2)} - 2(r^{(2)} + \delta_t^{(2)} + \delta_f^{(2)} + \delta_0^{(2)}) \quad (29b)$$

The equations for the first and second collection fibers demonstrate that the light scattered or emitted and collected by the first and second collection fibers for one particle will be different when the particle is not perfectly centered in the channel, and/or if the first and second collection fibers have different parameters and/or are not perfectly aligned. It is thus not possible to simply add the collected light, and an algebraic analysis including relative position information for the two collection fibers is required.

The length of the combined light collected will be obtained by:

$$\gamma_{total}^{(1+2)} = \text{MAX}(x_4^{(1)}, x_4^{(2)}) - \text{MIN}(x_1^{(1)}, x_1^{(2)}) \quad (32)$$

The duration of the plateau of combined collected light will then be obtained by:

$$\gamma_{plateau}^{(1+2)} = \text{MIN}(x'_1{}^{(1)}, x'_1{}^{(2)}) - \text{MAX}(x'_4{}^{(1)}, x'_4{}^{(2)}) \quad (33)$$

Analysis of Transition Zones

Transition zones correspond to the intervals where the intensity of light collected increases or decreases, excluding the plateau, which is of a relatively constant light intensity.

In a first approximation, the particle is considered to be Lambertian, i.e. of constant radiance (W/m²·sr). Considering the collection window of the collection fiber and the distance between the light emitting particle and the collection fiber, an angular dependence of the light emitted will be relatively small. For example, for an angular dependence of $\cos^4\theta_t$, $\cos^4\theta_t$, an intensity of 95% at $l_1$ of the intensity in $\mathcal{E}$ is obtained. In the calculation of the signal intensity in the transition zones, the present description will be limited to consider only the intersection of a circle of radius $(l_1-x)$, centered at x x, with a circle of radius R positioned at $(x=L-\in)$. A normalized intensity $I^{(1)}$ $I^{(1)}$ in the first collection fiber is obtained by the ratio of the area of the intersection over the normalized total surface of the circle of radius $(l_1-x)$:

$$I^{(1)} = \frac{A_{inter}^{(1)}(x)}{A_{total}^{(1)}} \quad (34)$$

where:

$$A_{inter}^{(1)}(x) = \quad (35)$$
$$R^{(1)^2}\cos^{-1}\left(\frac{d^2+R^{(1)^2}-r^{(1)^2}}{2dR^{(1)}}\right) + r^{(1)^2}\cos^{-1}\left(\frac{d^2-R^{(1)^2}+r^{(1)^2}}{2dr^{(1)}}\right) -$$
$$\sqrt{\left(\frac{d+r^{(1)}+}{R^{(1)}}\right)\left(\frac{d+r^{(1)}-}{R^{(1)}}\right)\left(\frac{d-r^{(1)}+}{R^{(1)}}\right)\left(\frac{-d+r^{(1)}+}{R^{(1)}}\right)}$$

$$A_{total}^{(1)} = \pi r^{(1)^2} \quad (36)$$

$$d = (L - \varepsilon - x) \quad (37)$$

$$r^{(1)} = (l_1^{(1)} - x) \quad (38)$$

Similar normalization can be performed for the second collection fiber and hence obtain a value for the total light intensity $I^{(1+2)}$ detected:

$$I^{(1+2)} = \frac{A_{inter}^{(1)}(x)}{A_{totale}^{(1)}} + \frac{A_{inter}^{(2)}(x)}{A_{totale}^{(2)}} \quad (39)$$

The previous set of equations (1 to 39) defines the relative relationship between the optical characteristics, the proportions and positions of the excitation fiber, the channel and collection fiber to generate non-Gaussian pulses by transiting particles in the interaction zone.

The present flow cell offers many advantages compared to prior art flow cells:

Configuration of the present flow cell uses optical parameters that maximize signal strength while minimizing noises sources. If the parameters of the excitation, channel and collection fibers are not selected according to the above formalism and left unconstrained, such as in prior art flow cell, for example as described in U.S. Pat. No. 7,835,599, completely arbitrary temporal profile will be generated. These temporal profiles could be Gaussian or Gaussian-like and therefore difficult to numerically process or unyielding of the particles properties. Using the present flow cell thus provides impressive performances over prior art flow cells, in addition to improving robustness and allowing a decrease in production costs by simplifying hardware and software requirements necessary to extract the characteristics of the particles to be analyzed.

Having the excitation fiber and the collection fiber characteristics selected, proportioned and positioned in regard to each other to generate and collect light of non-Gaussian temporal intensity profile further provides advantages for the design of the optics collection system by requiring fewer treatments thereto. For example, low-pass filters can be removed, as the light collected is intrinsically heavily low-pass filtered by the configuration of the flow cell.

Non-Gaussian temporal light collected further allows simpler design of the optical detection system, by providing results of quality with only trans-impedance amplifier compensation.

By selecting the excitation fiber, the channel and the collection fiber characteristics, proportions, and positioning relative to each other in accordance with the above formalism, it is possible to not only generate non-Gaussian temporal intensity profile impulsions and simplify signal processing, but to optimize the generated non-Gaussian temporal intensity profile impulsions as a function of the particles to be characterized.

Preliminary simulation of the light collected by the collection fibers of the present flow cell optimized according to the above formalism showed that the light collected for a particle has a flat portion, with transition zones from the background level up to that flat portion.

Treatment and Analysis of Non-Gaussian Temporal Impulsions

By carefully selecting the excitation fiber, the channel and the collection fibers characteristics and geometries and positioning them properly with respect to one another in accordance with equations 1 to 39, it was experimentally demonstrated that non-Gaussian temporal intensity profile light could be generated and collected by the collection fibers. The resulting impulsions generated in the flow cell were not Gaussian as known in the prior art, but trapezoidal over time: a linear rise, a flat top and a linear fall, having a rise/top and fall/top ratio of approximately 1:2.

Figure 10:
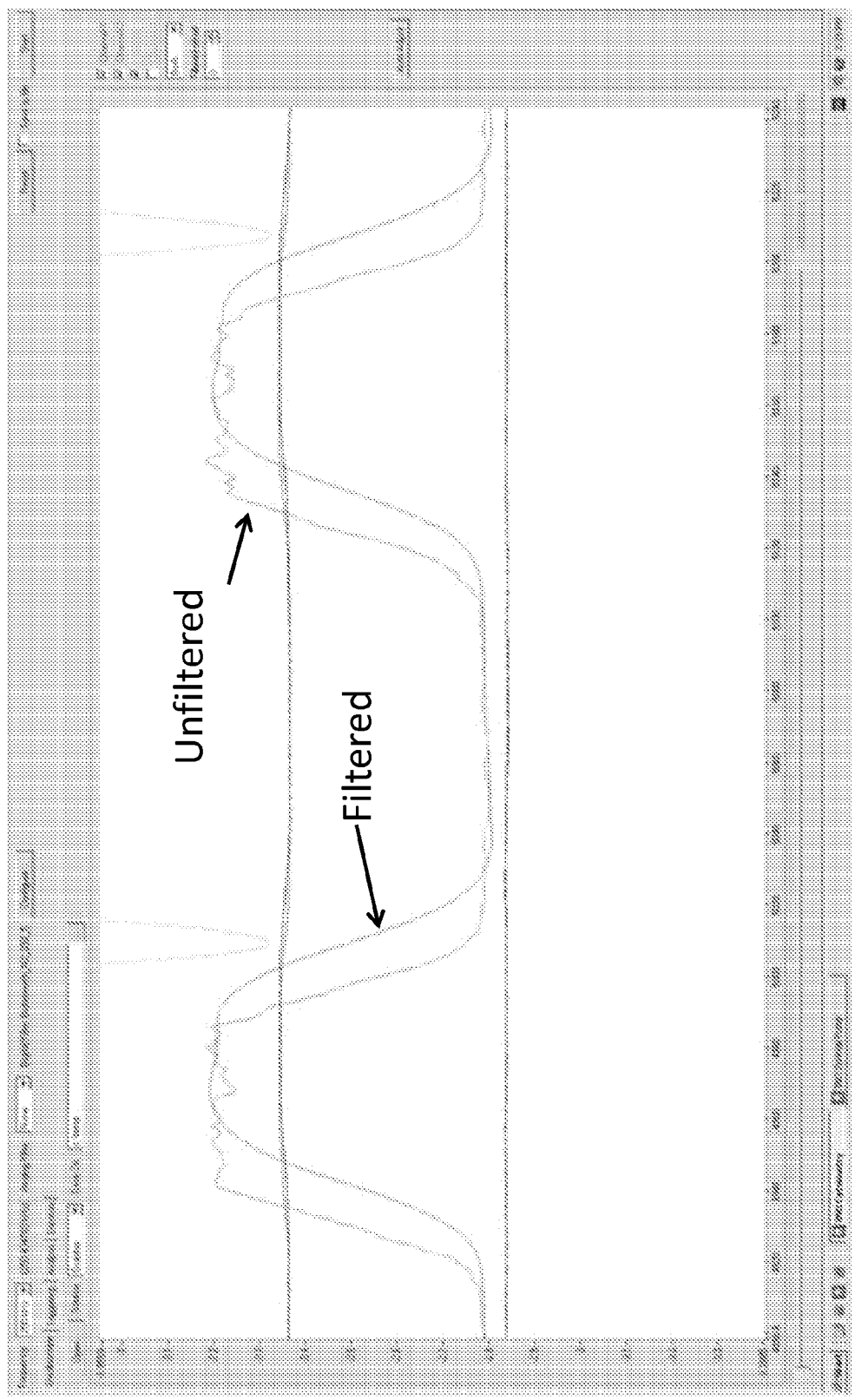
FIG. 10 is graph showing simulation results for unfiltered collected light (trapezoidal temporal intensity profile) and $4^{th}$ order 5 KHz filtered collected light (rounded shape)

Reference is now made to FIG. 10, which depicts simulation results of unfiltered collected light, represented by the trapezoidal impulsions, and $4^{th}$ order 5 KHz filtered collected light, represented by the rounded impulsions.

Thus the non-Gaussian temporal collected light provides a lot of information about the particles. In order to better extract information contained in the non-Gaussian temporal collected light, techniques of trapezoidal temporal pulse shaping, trapezoidal carrier pulse train shaping and filtering are used. Trapezoidal shaping is simple to perform with analog circuits, providing a flat top segment that is useful for accurate measurement while reasonably limiting the required signal bandwidth, thereby reducing noise. Trapezoidal carrier impulsion train shaping closely approaches the cosine shaping used for Gaussian signals, but is much simpler to perform.

For flow cell and flow cytometry, trapezoidal and/or triangle collected light provides very interesting properties compared to the Gaussian collected light of prior art flow cells and flow cytometers. Gaussian signal processing is mostly done digitally, due to its inherent complexity in the time domain. In order to increase resolution and/or precision of characteristics extracted from Gaussian signals, the analog impulsion is sampled many times to apply digital filters, so as to determine the amplitude, area and width of the resulting signal. As known in the art, the ideal filter for a given signal is a filter that has exactly the same frequency response as the signal itself, i.e. a matched filter. In digital signal processing, matched filtering is achieved by performing a convolution of the signal of interest by a filter kernel having the same ideal shape. Thus, for an impulsion sampled N times, the filter kernel requires N multiplications and additions for every new sample that is to be processed. Additionally, to get the best possible precision for height, area and width values determination, a non-linear fitting over the impulsion samples is required to extract the characterizing information. All these considerations represent resource-intensive signal processing operations. For example, if the selected algorithm uses 64-sample per Gaussian pulse, signal processing requires 128 operations times 64 samples, for a total of 8,192 operations. Using recursive approximation filters can reduce this complexity but pulse fitting for accurate pulse parameter determination such as amplitude, width and area is still processing-intensive.

For non-Gaussian temporal collected light, the top portion of the impulsion may be filtered by simply using a moving-sum filter requiring one addition and one subtraction for every subsequent sample. For example, if the top portion of the non-Gaussian temporal impulse represents 50% of the impulse width, computing requirements can be drastically reduced, i.e. cut by a factor 2. For the same example as above, the Non-Gaussian pulse sampling would require only 64 samples times 2 operations for a total of 128 operations, that is, at least a 64-fold decrease in signal processing resources. In addition and contrary to the Gaussian pulses, determination of amplitude, width and area of non-Gaussian pulses such as, for example, trapezoidal impulsions, is trivial since it relies on simple averaging techniques and linear fitting.

Cartridge with Integrated Microfluidic System

In another embodiment, a set of removable flow cell cartridges, each having different specific geometries and combinations of excitation fiber, channel and collection fibers could be provided. The cartridges, which could be provided either as single-use disposable devices or as reusable components, could be used to perform either consecutively or concurrently characterization of several types of sample solutions containing various particles. Each of the flow cell cartridges could be merely used as a generic and versatile measurement device for the characterization of multiple sample solutions, or combined with an embedded microfluidic system and reagents used to prepare a specific solution sample before measurements in the context of a dedicated assay. Alternatively, a single cartridge could provide a multiplicity of low cells therein, all of which can either be identical or non-identical, and be used sequentially or in parallel. All of the above embodiments provide means to accommodate a great diversity of tests with improved accuracy and/or throughput while reducing processing requirements, on a single readout apparatus.

Method

Figure 11:
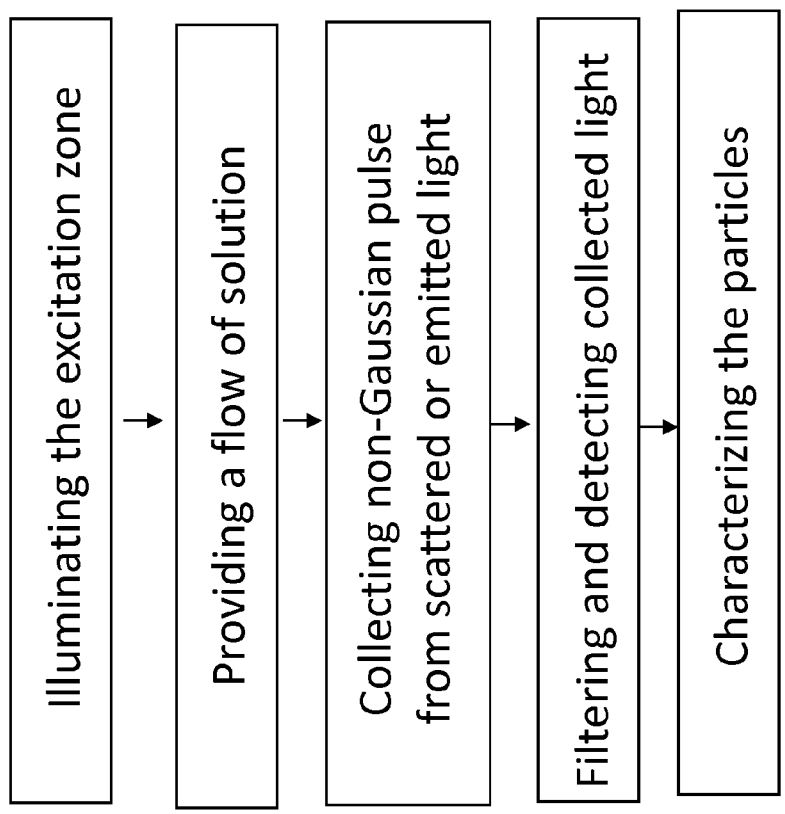
FIG. 11 is a schematic representation of the present method.

Reference is now made to FIG. 11, which is an exemplary sequential representation of the present method. First, an excitation zone within the flow cell is illuminated. When the excitation zone is illuminated, a flow of the sample solution containing the particles to be characterized is provided and channeled within the channel of the excitation fiber. Light scattered and/or emitted in the form of non-Gaussian temporal impulsions by the particles is then collected. The method further comprises performing a filtering-and-derivating operation on the non-Gaussian temporal impulsions to complete the characterization of the particles.

In addition, the method offers the flexibility of changing a flow cell cartridge for another one having a different set of characteristics in order to increase the precision of the extracted particle characteristics. Since the non-Gaussian temporal intensity profile of the light collected depends on the specific flow cell characteristics, testing the same sample solutions with different cartridges could significantly increase the precision of particles characterization, while reducing signal processing requirements.

Thus, by using flow cells with different characteristics, it is possible to optimize the non-Gaussian temporal intensity profile of the collected light and select the flow cell which yields the best results. This feature allows higher accuracy for particle characterization, a distinctive feature impractical for flow cells described in prior art. Those of ordinary skill in the art will realize that the description of the present flow cell, cartridge and method are illustrative only and are not intended to be in any way limiting. Other embodiments will readily suggest themselves to such persons with ordinary skill in the art having the benefit of the present disclosure.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A flow cell for characterizing particles in a sample solution, the flow cell comprising:
   an excitation fiber having a core for transporting an excitation light, the excitation fiber defining a channel transversal to its core for directing a flow of the sample solution there through; and
   at least one collection fiber adjacent to the channel, the at least one collection fiber collecting light scattered or emitted by the particles flowing through the channel and excited by the excitation light;
   wherein the excitation fiber, the channel and the at least one collection fiber characteristics are selected and the excitation fiber, the channel and the at least one collection fiber are proportioned and positioned relative to each other so as to allow the scattered or emitted light to enter and be guided by the at least one collection fiber, the scattered or emitted light forming a circle at an entrance of the at least one collection fiber, the circle having a diameter defined by a numerical aperture of the at least one collection fiber, the characteristics, proportions and positions of the excitation fiber, of the channel and of the at least one collection fiber meeting a condition to generate collected light of a non-Gaussian temporal intensity profile, the condition being:

$$\frac{r + NA\left[\dfrac{(2t-r)}{\sqrt{n_t^2 - NA^2}} + \dfrac{R'-t}{\sqrt{n_f^2 - NA^2}} + \dfrac{g}{\sqrt{n_0^2 - NA^2}}\right]}{R} < 1$$

wherein:
   NA is equal to $\sqrt{n_1^2 - n_2^2}$ and is the numerical aperture of the at least one collection fiber,
   $n_1$ is a refractive index of a core of the at least one collection fiber,
   $n_2$ is a refractive index of a cladding of the at least one collection fiber,
   $n_f$ is a refractive index of the core of the excitation fiber,
   $n_t$ is a refractive index of the sample solution in the channel,
   $n_o$ is a refractive index of a medium in a gap between an endface of the at least one collection fiber and the excitation fiber,
   g is a size of the gap between the endface of the at least one collection fiber and the excitation fiber,
   t is a half-width of the channel in a direction perpendicular to the endface of the at least one collection fiber,
   R' is a half-width of the excitation fiber core in the direction perpendicular to the endface of the at least one collection fiber,
   R is a half-width of the at least one collection fiber in a direction parallel to a flow of the sample solution through the channel in the excitation fiber, and
   r is a half-width of the particles in the direction parallel to a flow of the sample solution through the channel in the excitation fiber.

2. The flow cell of claim 1, wherein the excitation fiber, the channel and the at least one collection fiber characteristics are selected and the excitation fiber, the channel and the at least one collection fiber are proportioned and positioned relative to each other so as to meet the condition to generate collected light of a non-Gaussian temporal intensity profile for a range of particle sizes.

3. The flow cell of claim 1, wherein the excitation fiber, the channel and the at least one collection fiber characteristics are selected and the excitation fiber, the channel and the at least one collection fiber are proportioned and positioned relative to each other so as to meet the condition to generate collected light of a non-Gaussian temporal intensity profile for a range of wavelengths.

4. The flow cell of claim 1, wherein the excitation fiber, the channel and the at least one collection fiber characteristics are selected and the excitation fiber, the channel and the at least one collection fiber are proportioned and positioned relative to each other so as to meet the condition to generate collected light of a non-Gaussian temporal intensity profile for a range of particle sizes and wavelengths.

5. The flow cell of claim 1, wherein the excitation fiber the channel and the at least one collection fiber characteristics are selected and the excitation fiber, the channel and the at least one collection fiber are proportioned and positioned relative to each other so as to generate collected light of a trapezoidal or triangular temporal intensity profile for a range n of particle sizes and wavelengths.

6. The flow cell of claim 1, wherein the excitation fiber and the at least one collection fiber are implemented as a removable flow cell cartridge.

7. The flow cell of claim 1, comprising two collection fibers diametrically disposed on each side of the excitation fiber.

8. The flow cell of claim 7, wherein the excitation fiber and the two collection fibers are implemented as a removable flow cell cartridge to be coupled to a light source and a detection system.

9. The flow cell of claim 1, wherein the excitation fiber further comprises a reflective surface at an extremity thereof opposite to a light source.

10. The flow cell of claim 7, wherein the excitation fiber and the two collection fibers are implemented as a removable flow cell cartridge, and wherein the excitation fiber further comprises a reflective surface at an extremity of the excitation fiber opposite to a light source.

11. The flow cell of claim 1, wherein the excitation fiber has a square or rectangular cross section.

12. The flow cell of claim 1, wherein the excitation fiber is made of glass, plastic or an other substantially transparent guiding material.

13. A method for characterizing particles in a sample solution, the method comprising:
   providing a flow of the sample solution containing particles in a channel of an excitation fiber;
   providing excitation light in the excitation fiber so as to illuminate the particles;
   collecting, in a collection fiber, non-Gaussian temporal scattered and/or emitted light pulses by the illuminated particles;
   filtering and detecting the collected non-Gaussian temporal light pulses so as to identify at least one characteristic of the particles;
   wherein the excitation fiber, the channel and the collection fiber characteristics are selected and the excitation fiber, the channel and the collection fiber are proportioned and positioned relative to each other so as to allow the scattered or emitted light to enter and be guided by the collection fiber, the scattered or emitted light forming a circle at an entrance of the collection fiber, the circle having a diameter defined by a numerical aperture of the collection fiber, the characteristics, proportions and positions of the excitation fiber, of the channel and of the collection fiber meeting a condition to generate collected light of a non-Gaussian temporal intensity profile, the condition being:

$$\frac{r + NA\left[\dfrac{(2t-r)}{\sqrt{n_t^2 - NA^2}} + \dfrac{R'-t}{\sqrt{n_f^2 - NA^2}} + \dfrac{g}{\sqrt{n_0^2 - NA^2}}\right]}{R} < 1$$

wherein:
 NA is equal to $\sqrt{n_1{}^2 - n_2{}^2}$ and is the numerical aperture of the collection fiber,
 $n_1$ is a refractive index of a core of the collection fiber,
 $n_2$ is a refractive index of a cladding of the collection fiber,
 $n_f$ is a refractive index of the core of the excitation fiber,
 $n_t$ is a refractive index of the sample solution in the channel,
 $n_o$ is a refractive index of a medium in a gap between the collection and excitation fibers,
 g is a size of the gap between the endface of the collection fiber and the excitation fiber,
 t is a half-width of the channel in a direction perpendicular to the endface of the collection fiber,
 R' is a half-width of the excitation fiber core in the direction perpendicular to the endface of the collection fiber,
 R is a half-width of the collection fiber in a direction parallel to a flow of the sample solution through the channel in the excitation fiber, and
 r is a half-width of the particles in the direction parallel to a flow of the sample solution through the channel in the excitation fiber.

14. The method of claim 13, wherein the excitation fiber, the channel and the collection fiber characteristics are selected and the excitation fiber, the channel and the collection fiber are proportioned and positioned relative to each other so as to meet the condition to generate collected light of a non-Gaussian temporal intensity profile for a range of particle sizes.

15. The method of claim 13, wherein the excitation fiber, the channel and the collection fiber characteristics are selected and the excitation fiber, the channel and the collection fiber are proportioned and positioned relative to each other so as to meet the condition to generate collected light of a non-Gaussian temporal intensity profile for a range of wavelengths.

16. The method of claim 13, wherein the excitation fiber, the channel and the collection fiber characteristics are selected and the excitation fiber, the channel and the collection fiber are proportioned and positioned relative to each other so as to meet the condition to generate collected light of a non-Gaussian temporal intensity profile for a range of particle sizes and wavelengths.

17. The method of claim 13, wherein the excitation fiber, the channel and the collection fiber characteristics are selected and the excitation fiber, the channel and the collection fiber are proportioned and positioned relative to each other so as to generate collected light of a trapezoidal or triangular temporal intensity profile for a range of particle sizes and wavelengths.

18. The method of claim 13, wherein the collection is performed by two collection fibers diametrically positioned on each side of the excitation fiber and facing an excitation zone.

19. The method of claim 13, wherein the excitation fiber, the channel and the one or several collection fibers are implemented as a removable flow cell cartridge.

20. A flow cytometer for characterizing particles in a sample solution, the flow cytometer comprising:
 a light source for generating an excitation light; and
 a flow cell comprising an excitation fiber and at least one collection fiber, the excitation fiber having a core for transporting the excitation light, the excitation fiber defining a channel transversal there through for channeling a flow of the sample solution, the at least one collection fiber being located proximate to the channel;
 wherein, the excitation fiber, the channel and the at least one collection fiber characteristics are selected and the excitation fiber, the channel and the at least one collection fiber are proportioned and positioned relative to each other so as to allow the scattered or emitted light to enter and be guided by the at least one collection fiber, the scattered or emitted light forming a circle at an entrance of the at least one collection fiber, the circle having a diameter defined by a numerical aperture of the at least one collection fiber, the characteristics, proportions and positions of the excitation fiber, of the channel and of the at least one collection fiber meeting a condition to generate collected light of a non-Gaussian temporal intensity profile, the condition being:

$$\frac{r + NA\left[\dfrac{(2t-r)}{\sqrt{n_t^2 - NA^2}} + \dfrac{R'-t}{\sqrt{n_f^2 - NA^2}} + \dfrac{g}{\sqrt{n_0^2 - NA^2}}\right]}{R} < 1$$

wherein:
 NA is equal to $\sqrt{n_1{}^2 - n_2{}^2}$ and is the numerical aperture of the at least one collection fiber,
 $n_1$ is a refractive index of a core of the at least one collection fiber,
 $n_2$ is a refractive index of a cladding of the at least one collection fiber,
 $n_f$ is a refractive index of the core of the excitation fiber,
 $n_t$ is a refractive index of the sample solution in the channel,
 $n_o$ is a refractive index of a medium in a gap between the collection and excitation fibers,
 g is a size of the gap between the endface of the at least one collection fiber and the excitation fiber,
 t is a half-width of the channel in a direction perpendicular to the endface of the at least one collection fiber,
 R' is a half-width of the excitation fiber core in the direction perpendicular to the endface of the at least one collection fiber,
 R is a half-width of the at least one collection fiber in a direction parallel to a flow of the sample solution through the channel in the excitation fiber, and
 r is a half-width of the particles in the direction parallel to a flow of the sample solution through the channel in the excitation fiber.

21. The flow cytometer of claim 20, further comprising an optical detection system and a signal processing device for performing a filter-and-derivative procedure on samples of the collected light.

* * * * *

UNITED STATES PATENT AND TRADEMARK OFFICE
CERTIFICATE OF CORRECTION

PATENT NO. : 8,736,837 B2  
APPLICATION NO. : 13/968744  
DATED : May 27, 2014  
INVENTOR(S) : Nolet et al.

It is certified that error appears in the above-identified patent and that said Letters Patent is hereby corrected as shown below:

In the Claims

Claim 1, Column 15, line 43, "NA is equal to $\sqrt{n_1{}^2 - n_2{}^n}$ and"

should read -- NA is equal to $\sqrt{n_1{}^2 - n_2{}^2}$ and --.

Signed and Sealed this  
Twenty-first Day of April, 2015

Michelle K. Lee  
*Director of the United States Patent and Trademark Office*